United States Patent [19]

Fahim

[11] 4,309,989

[45] * Jan. 12, 1982

[54] TOPICAL APPLICATION OF MEDICATION BY ULTRASOUND WITH COUPLING AGENT

[75] Inventor: Mostafa S. Fahim, Columbia, Mo.

[73] Assignee: The Curators of the University of Missouri, Columbia, Mo.

[ * ] Notice: The portion of the term of this patent subsequent to Nov. 12, 1998, has been disclaimed.

[21] Appl. No.: 933,205

[22] Filed: Aug. 14, 1978

Related U.S. Application Data

[63] Continuation of Ser. No. 656,143, Feb. 9, 1976, abandoned.

[51] Int. Cl.$^3$ ................... A61K 33/02; A61K 33/30; A61M 37/00; A61H 23/00
[52] U.S. Cl. ................... 128/24 A; 128/260; 128/65; 424/145; 424/289
[58] Field of Search ................ 128/24 A, 65, 260; 424/131, 145

[56] References Cited

U.S. PATENT DOCUMENTS

| | | | |
|---|---|---|---|
| 2,254,636 | 9/1941 | Vangunten | 424/131 |
| 3,102,535 | 9/1963 | Dailey | 128/24 A |
| 3,219,029 | 11/1965 | Richards et al. | 128/24 A |
| 3,760,799 | 9/1973 | Crowson | 128/24 A |
| 3,828,769 | 8/1974 | Mettler | 128/24 A |

OTHER PUBLICATIONS

The Dispensatory of the U.S.—Osol–Farrar, p. 1518.
The Merck Manual 12th Edition, pp. 33–35.

*Primary Examiner*—Robert W. Michell
*Assistant Examiner*—Nancy A. B. Swisher
*Attorney, Agent, or Firm*—Grace J. Fishel

[57] ABSTRACT

A method of topically applying an effective medication in an emulsion coupling agent by ultrasound. More particularly, a method of treating a skin condition by applying a medication in an emulsion coupling agent and massaging it into the affected area with ultrasonic vibrations thereby causing the medication to penetrate into the skin. Specifically, a method and composition for the treatment of Herpes Simplex Type 1 and Type 2 lesions. Also specifically, a method and composition for the treatment of demidox mites.

6 Claims, No Drawings

TOPICAL APPLICATION OF MEDICATION BY ULTRASOUND WITH COUPLING AGENT

This is a continuation of application Ser. No. 656,143, filed Feb. 9, 1976, now abandoned.

The present invention relates to a method of treating a skin condition with an effective medication by applying it with ultrasonic vibrations through a coupling agent such as oil. More particularly, the present invention relates to a method for applying an effective antiviral drug to Herpes Simplex lesions by ultrasound and to the compositions thereof. It also relates to a method for applying an effective medication to demidox mites by ultrasound and to the composition thereof.

Herpes Simplex is an infectious disease having two major serotypes of the causative virus. As a general rule, Type 1 virus is responsible for oral herpes and other skin lesions above the waist. Type 2 virus, on the other hand, is usually responsible for genital herpes, other skin lesions below the waist and for neonatal herpes.

The two serotypes differ in their cytopathic effect on cells in tissue culture, virulence for laboratory animals, behavior on embryonated chicken eggs and, as mentioned above, their usual site on the body. Both types, however, can occur outside of its usual location and with changing mores, more and more cases of genital herpes are caused by Type 1 virus. Occasionally, neonatal herpes is also caused by Type 1 virus. The occurrence of genital herpes is on the rise, particularly among young people. The disease is classified as venereal and is regarded as a serious medical problem.

The clinical manifestations of oral and genital herpes vary from individual to individual but the disease usually appears as a series of vesicles. In the case of oral herpes, the disease may manifest itself as fever blisters or as lesions on the lips or face. The lesions are self-limiting and usually heal in about 7 to 14 days but are troublesome to the patient causing itching and burning and are somewhat disfiguring.

Genital herpes is more serious and can be very painful, especially in women. In females, genital herpes can be diffuse and involve the entire vulva, orifice of the vagina, cervix and cervical end of the vagina. Bilateral inguinal lymphadenopathy is the rule. When the vesicles are diffuse, the majority of women have systemic manifestations such as chill, fever and general aching. Dysuria and dyspareunia are common. Occasionally, there is acute urinary retention due to reflex spasm of the urethral sphincter.

In males, genital herpes usually consists of vesicles on the glans of the penis or on the penis. The lesions may be painful but systemic manifestations are uncommon.

In most patients overt recurrent Herpes Simplex lesions do not appear but in other individuals, recurrences are common. The duration and frequency of reactivation of the infection varies considerably, but the course of the disease tends to remain fairly constant in any given individual. These recurrences may be provoked by excitants, such as fever, sunshine, gastrointestinal upsets, mechanical trauma, allergy, repressed anxiety of hostility or menstrual periods and are known to be more common during pregnancy. Frequent recurrences are distressing to the patient, and for women genital herpes takes on additional significance because of the suspected association of Type 2 Herpes Simplex and carcinoma of the cervix and because of the serious nature of neonatal herpes transmitted from mother to infant during late pregnancy and delivery.

In the past, ultrasound has been used to relieve symptoms of musculoskeletal disorders and to clean and treat open wounds. Numerous treatments for Herpes Simplex lesions have been tried. In the case of genital herpes, one of the more common methods involves painting infected areas with acridine dyes and then exposing them to light. This treatment has been criticised as a potential danger in itself because the inactivated viruses may still be able to transform normal mammalian cells into cells with new inheritable characteristics and with loss of contact inhibition, which characteristics are often associated with a malignant potential.

In view of the above, among the several objects of the present invention is the provision of a method for treating a skin condition with an effective medication by applying it with ultrasonic vibrations through a coupling agent such as oil. More specifically, the object of the present invention is the provision of a method for treating Herpes Simplex involving the application of an effective antiviral drug such as urea to the affected area by ultrasound, said method facilitating the administration of the antiviral drug intracellularly. Other objects and features will be in part apparent and in part pointed out hereinafter.

The invention accordingly comprises the methods and compositions hereinafter described, the scope of the invention being indicated in the following claims.

In accordance with the present invention, skin conditions in man or other animals are treated with an effective medication which is applied to the affected area and then directly micromassaged therein by ultrasonic vibrations through a coupling agent such as oil.

More particularly, lesions caused by Herpes Simplex are treated with an antiviral drug which is effective against Herpes Simplex and directly applied with ultrasonic vibrations.

Suitable antiviral drugs effective for the present purpose include urea, idoxuridine, amantadine, methisazone, cytarabine, interferons or the like. In the preferred form, a medicament containing an effective amount of the antiviral drug is first made up. In general, the medicament contains from about 5 to about 40 percent by weight of the antiviral drug. In treating Herpes Simplex, urea is often selected as the antiviral drug because it is also effective against cancer. When the drug is urea and the medicament is for treatment of oral herpes, it generally contains from about 10 percent by weight to about 30 percent by weight of urea, and when it is for treatment of genital herpes, it contains from about 10 percent by weight to about 40 percent by weight of urea.

More preferred medicaments for treatment of oral Herpes Simplex contain from about 20 percent to about 30 percent by weight of urea and for treatment of genital Herpes Simplex contain from about 30 percent by weight to about 40 percent by weight. Especially preferred are medicaments containing about 30 percent by weight of urea for treatment of oral herpes or genital herpes.

Usually, the medicament includes other materials to accelerate or otherwise promote healing. When the medicament is for oral application, such materials include zinc oxide, tannic acid, menthol, ethyl alcohol or the like. For this purpose, the zinc oxide is present in an amount from about 0.5 percent by weight to about 3 percent by weight, preferably from about 1 percent by weight to about 3 percent by weight and more preferably from about 1.5 percent by weight to about 2 percent by weight.

Zinc compounds such as zinc oxide are included because zinc amplifies the mechanical effects of the ultrasonic vibrations to break the viral membranes so that the antiviral drug is administered intracellularly. Moreover, zinc oxide functions as an astringent, as a corrosive to promote healing and as a mild antiseptic.

Tannic acid is included because it is an astringent and precipitates protein with heavy metal ions such as zinc. Since Herpes Simplex viruses are protein, the combined effect of zinc oxide and tannic acid is to kill the virus.

Menthol is added to the lip formation because it gives a cool feeling and relieves itching. Ethyl alcohol is included as a mild antiseptic because patients often scratch their blisters and cause secondary infection therein.

The tannic acid is present in an amount from about 0.5 percent by weight to about 2 percent by weight, preferably from about 0.5 percent by weight to about 1.5 percent by weight and more preferably from about 1 percent by weight to about 1.5 percent by weight.

The menthol is present in an amount from about 0.25 percent by weight to about 1 percent by weight, preferably from about 0.25 percent by weight to about 0.75 percent by weight and more preferably from about 0.30 percent by weight to about 0.50 percent by weight.

The ethyl alcohol is present in an amount from about 0.30 percent by weight to about 1.0 percent by weight, preferably from about 0.30 percent by weight to about 0.75 percent by weight and more preferably from about 0.30 percent by weight to about 0.50 percent by weight.

When the medicament is for genital application, the materials to accelerate or otherwise promote healing are the same as for oral application except that menthol and ethyl alcohol are eliminated. In this case, the zinc oxide is present in an amount from about 1 percent by weight to about 5 percent by weight, preferably from about 2 percent by weight to about 4 percent by weight and more preferably from about 2.5 percent by weight to about 3 percent by weight.

The tannic acid is present in an amount from about 1 percent by weight to about 5 percent by weight, preferably from about 2 percent by weight to about 4 percent by weight and more preferably from about 3 percent by weight to about 4 percent.

Since ultrasound does not transmit through air, the medicament must provide a coupling between the ultrasonic applicator and the skin to be treated. For this purpose, the medicament usually contains oil or similar material so there are no air gaps between the applicator and the underlying skin.

The particular coupling agent selected is preferably non-staining, non-irritating and slow drying. The nature and amount of coupling agent is selected so that the resultant paste or gel is not so fluid at body temperature that is flows from between the ultrasonic applicator and the skin resulting in poor or no ultrasonic coupling.

Suitable coupling agents include mixtures of mineral oil and glycerin or the like but the preferred coupling agent is HEB cream sold by Barnes Hind Company. This material is a mixture of cetyl alcohol, stearyl alcohol, white petrolatum, mineral oil and propylene glycol. When the medicament is for oral application and the coupling agent is HEB cream, the coupling agent is present in an amount from about 65 to about 70, preferably from about 65 to about 67 and more preferably from about 65 to 66 percent by weight. When the medicament is for genital application and the coupling agent is HEB cream, the coupling agent is present in an amount from about 60 percent to about 70 percent by weight, preferably from about 60 to about 68 and more preferably from about 60 to 65. Other formulations based on other coupling agents can be readily determined by one skilled in the art given the properties required thereof as described above.

The medicament is made up by combining the above-mentioned materials in the amounts described and by blending them until a paste or gel is formed. Since the medicament is shelf stable, it may be prepared in advance and stored.

When the medicament is ready for use, the patient is comfortably positioned and his lesions examined. An amount of medicament is rubbed onto the area to be treated in an amount sufficient to assure good coupling between the ultrasonic applicator and the skin to be treated.

The medicament is then micromassaged into the affected area by ultrasonic vibrations. For this purpose, an ultrasonic applicator is slowly moved back and forth over the lesions, either in a rotary or transverse direction, in order to reduce the concentration of energy at any given point. The pressure applied through the applicator is light but is firm enough to maintain good coupling. In treating patients having lesions which are particularly painful and sensitive to heat, the ultrasonic applicator, which includes a transducer within an applicator housing, is preferably water cooled.

The length of the treatment, output frequency of the ultrasonic generator coupled to the applicator and power level at the applicator surface will vary in the individual case and is up to the physician. Preferably, however, the output frequency of the generator is about 1000 KHZ and the power level at the applicator head is about 1.0 to 3.0 watts per sq. cm. A suitable ultrasonic generator for this purpose is manufactured by Whitewater Electronics, Inc. and has a frequency of 1100 KHZ±10 KHZ, a continuous power output of 0 to 32 watts and an effective power level at the applicator head of 3.0 watts per sq. cm.

The frequency and number of treatments is determined individually at the discretion of the physician. Often to begin with, treatments are given daily for 2 to 3 minutes and then reduced in frequency when desired effects are obtained. It is not unusual, however, that only one treatment is necessary before beneficial effects become apparent.

The following examples illustrate the invention.

EXAMPLE 1

An effective medicament (HERPIGON LOTION I) for the treatment of Herpes Simplex Type 1 lesions by ultrasound was prepared by blending the following materials:

| Ingredient | Percent by Weight |
| --- | --- |
| Urea | 30 |
| Zinc oxide | 2 |
| Tannic acid | 1 |
| Menthol | 0.5 |
| HEB cream | 66 |
| Ethyl alcohol | qs |

EXAMPLE 2

To demonstrate that ultrasonic vibrations cause HERPIGON LOTION I to penetrate tissues through the skin, sixty rats were chosen, their backs shaved and treated as follows:

Ten rats were selected for each of three tests in Group A. In each test, radioactive HERPIGON LOTION I was rubbed onto the shaved backs of the rats. As shown in Table A, in Test 1 the radioactive component of the HERPIGON LOTION I was tannic acid, in Test 2 it was urea and in Test 3 it was a combination of tannic acid and urea. Otherwise, the HERPIGON LOTION I used in these tests was prepared as in Example 1.

TABLE A

| | Radioactive Component |
|---|---|
| Test 1, Test 4 | Tannic acid ($H^3$) |
| Test 2, Test 5 | Urea ($C^{14}$) |
| Test 3, Test 6 | Tannic acid ($H^3$) and Urea ($C^{14}$) |

Ten rats were selected for each of three tests in Group B. In each test, radioactive HERPIGON LOTION I was rubbed onto the shaved backs of the rats and micromassaged therein with ultrasound for about 5 minutes. An ultrasonic generator with a frequency of 1100 KHZ±10 KHZ was coupled to an ultrasonic applicator. The applicator head measured 2.5 sq. cm. and had an effective power level of 1 watt per sq. cm. As shown in Table A, the radioactive components of the HERPIGON LOTION I in Tests 4, 5 and 6 were the same as in Tests 1, 2 and 3, respectively.

All of the rats in Groups A and B were sacrificed and vertical sections 1 inch thick including the skin were taken from their back muscles. Slices were then made, fixed and analyzed by autoradiographic localization for penetration of the radioactive drugs. The results show that both radioactive urea and tannic acid are caused to enter the muscle to a depth of from about ½ inch to about 1 inch when they are applied with ultrasonic vibrations. When they are applied without vibrations, they remain on the surface of the skin and do not penetrate the muscle.

EXAMPLE 3

Ten subjects suffering oral herpes were chosen on the basis of visible evidence of active lesions on the lips, inside of the lips or mouth. Each had 3 or 4 vesicles and came in for treatment between 12 and 24 hours after appearance of the blisters. A sample was taken by cotton swab from the infected area of each subject and preserved in a special media for virus culture. The virus was identified as Herpes Simplex Type 1 by culture and by electron microscopy.

Five of the subjects were selected for a control group. They were treated by rubbing an ultrasonic applicator head as described in Example 2 over the infected area for two minutes. The control patients reported that itching continued for 4 to 7 days and that the blisters took from 7 to 12 days to disappear.

The other five subjects were selected for an active treatment group according to the present invention. An amount of HERPIGON LOTION I as prepared in Example 1 was applied to the lesions and the subjects were treated with ultrasound as described above. The blisters were treated on two consecutive days. The active treatment patients reported that itching stopped after 4 to 6 hours. Blisters were reported as having a healing crust after 12 to 18 hours and as disappeared after about 4 days.

EXAMPLE 4

An effective medicament (HERPIGON LOTION II) for the treatment of Herpes Simplex Type 2 lesions by ultrasound was prepared by blending the following materials:

| Ingredient | Percent by Weight |
|---|---|
| Urea | 30 |
| Zinc oxide | 3 |
| Tannic acid | 2 |
| HEB cream | 65 |

EXAMPLE 5

Twenty female subjects suffering from recurrent genital herpes at least three times in the preceding year were chosen. Each patient came in for treatment about 12 to 24 hours after appearance of the blisters as vesicles on the vulva and orifice of the vagina. A sample was taken by cotton swab from the infected area of each subject both before and after treatment and preserved in a special media for virus culture. The virus was identified as Herpes Simplex Type 2 by culture and by electron microscopy.

Five of the subjects were selected for a control group. Members of this group had 20 to 50 blisters and were treated by rubbing an ultrasonic applicator over the infected areas for three minutes. The particular applicator selected depended on the size of the infected area. Probe A measured 5 sq. cm., Probe B 2.5 sq. cm. and Probe C 1.5 sq. cm. Probe A was used if the blisters covered a wide area. In smaller areas, Probe B was used and in hidden areas such as beneath the clitoris or labia minora, Probe C was used. The ultrasonic generator coupled to the applicator had an output frequency of 1100 KHZ±10 KHZ and the power output was selected so that the effective power level at the applicator head, regardless of which one was selected, was 0 watts per sq. cm. The control "treatment" was applied once daily for three consecutive days. The control patients reported that itching and pain lasted for about a week to 10 days and that the blisters took 3 to 4 weeks to disappear. All of the subjects experienced recurrent infections within three months.

Another five subjects were selected as a group for treatment with ultrasound alone. Members of this group had 7 to 50 vesicular lesions and were treated as described above except that the power level at the applicator head was 1 watt per sq. cm., once daily for three consecutive days. On the third day of treatment, 60 percent of the virus had been killed as evidenced by the sample taken on the cotton swab. The ultrasound treatment group reported that itching and pain lasted about 4 days and that the blisters disappeared after about 18 to 20 days.

Five more of the subjects were selected for treatment with HERPIGON LOTION II alone. Members of this group had 10 to 50 vesicular lesions and were treated by rubbing HERPIGON LOTION II onto the infected areas twice a day for three days. On the third day of treatment, 65 percent of the virus had been killed. The HERPIGON LOTION II treatment group reported that itching lasted about 3 days and that the blisters disappeared after about 15 to 17 days.

The other five subjects were treated as follows. Members of this group had 10 to 50 vesicular lesions and were treated by rubbing HERPIGON LOTION II onto the infected areas and immediately micromassaging it therein with the probes described for the control group except that the power level at the applicator head was 1 watt per sq. cm. This treatment was applied once daily for three minutes on each of three consecutive days. On the third day of treatment, 100 percent of the virus had been killed at the site of the lesions. This treatment group reported itching stopped after 12 to 24 hours and blister disappearance after 5 to 7 days.

All twenty subjects were followed after treatment. As mentioned above, all of the control group had recurrent genital herpes infections within three months. Fifty percent of the subjects treated with ultrasound alone had recurrent infections within 5 months, 45 percent of the subjects treated with HERPIGON LOTION II alone had recurrent infections within 6 months but 100 percent of the subjects treated with HERPIGON LOTION II and ultrasound were still free from recurrent infections after one year.

EXAMPLE 6

Ten male subjects suffering genital herpes were chosen. Each had 2 to 6 vesicles on the glans of the penis or on the penis. No blisters were noted on the scrotum with the exception of one patient who had two blisters. A sample was taken by cotton swab from the infected areas of each subject and preserved in a special media for virus culture. The virus was identified as Herpes Simplex Type II by culture and by electron microscopy.

Five of the subjects were selected for a control group. They were treated by rubbing an ultrasonic applicator head such as Probe A or Probe B of Example 4 over the infected areas for three minutes. The power level at the applicator head was set for 0 watts per sq. cm. The control patients seldom reported itching but those who did said that it lasted about 3 days. Blisters took 2 weeks to disappear.

The other five subjects were selected for an active treatment group according to the present invention. An amount of HERPIGON LOTION II was applied to the lesions and the subjects were treated as described for the control group above except that the effective power level at the applicator head was 1 watt per sq. cm. These patients reported that itching (if initially present) stopped within 4 to 8 hours and that the blisters disappeared within 5 to 7 days.

EXAMPLE 7

An effective medicament (DEMIDOX SHAMPOO) for the treatment of demidox mites in dogs when applied with ultrasound was prepared by blending the following materials:

| Ingredient | Percent by Weight |
|---|---|
| Urea | 20 |
| Dimethyl sulfoxide | 10 |
| Glycerol | qs |

In general, effective DEMIDOX SHAMPOOS contain from about 10 to about 50 percent by weight of urea and from about 1 to about 20 percent by weight of dimethyl sulfoxide with the balance being made up by glycerol. When these shampoos are micromassaged into the infected areas with ultrasound as described for treatment of Herpes Simplex Type 1 to 2 lesions, the urea and dimethyl sulfoxide penetrate the tissues and kill the mite eggs. The glycerol acts as an ultrasound coupling agent and as a lubricant.

EXAMPLE 8

Seven dogs suffering with demidox were treated by rubbing an amount of DEMIDOX SHAMPOO as prepared in Example 7 onto the infected areas. These areas were then rubbed with an ultrasonic applicator for 5 to 7 minutes. An ultrasonic generator as described in Example 2 was set so that the effective power level at the applicator head was from about 1 to about 1.5 watts per sq. cm. The dogs were treated every other day for 20 days. All seven of the dogs were cured after 10 treatments.

In view of the above, it will be seen that the several objects of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. In the treatment of Herpes Simplex lesions, a method for the selective localized intracellular administration of a medication including urea and a zinc compound in a coupling agent, the urea and zinc compound being present in an effective amount, which comprises applying said medication to the affected area and massaging said medication therein with an ultrasonic applicator coupled to an ultrasonic generator, said applicator continuously vibrating at a frequency of at least 1,000 KHZ and having an effective power level from about 1 watt per sq. cm to about 3 watts per sq. cm for a time sufficient to obtain intracellular penetration of said medication without causing undo cell wall deterioration whereby the zinc amplifies the mechanical effects of the ultrasonic vibrations and the urea acts as an antiviral agent.

2. The method for treatment of Herpes Simplex lesions according to claim 1 wherein the medication further includes an astringent.

3. The method for treatment of Herpes Simplex lesions according to claim 2 wherein the urea is present in an amount from about 5 to about 40 percent by weight.

4. The method for treatment of Herpes Simplex lesions according to claim 3 wherein the lesions are Type 1 lesions and wherein the astringent is tannic acid, said urea being present in an amount from about 10 percent to about 30 percent by weight, said zinc compound is zinc oxide and is present in an amount from about 0.5 percent to about 3 percent by weight and said tannic acid is present in an amount from about 0.5 percent to about 2 percent by weight.

5. The method for treatment of Herpes Simplex Type 1 lesions according to claim 4 wherein the medication further includes menthol in an amount from about 0.25 percent to about 1 percent and ethyl alcohol in an amount from about 0.30 percent to about 1 percent by weight.

6. The method for treatment of Herpes Simplex lesions according to claim 3 wherein the lesions are Type 2 lesions and wherein the astringent is tannic acid, said urea being present in an amount from about 10 percent to about 40 percent by weight, said zinc compound is zinc oxide and is present in an amount from about 1 percent to about 5 percent by weight and said tannic acid is present in an amount from about 1 percent to about 5 percent by weight.

* * * * *